US009250186B2

(12) United States Patent
Farahi et al.

(10) Patent No.: US 9,250,186 B2
(45) Date of Patent: Feb. 2, 2016

(54) PROFILOMETRY SYSTEMS AND METHODS BASED ON ABSORPTION AND OPTICAL FREQUENCY CONVERSION

(71) Applicants: Faramarz Farahi, Charlotte, NC (US); Mehrdad Abolbashari, Charlotte, NC (US); Gelareh Babaie, Charlotte, NC (US)

(72) Inventors: Faramarz Farahi, Charlotte, NC (US); Mehrdad Abolbashari, Charlotte, NC (US); Gelareh Babaie, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 14/217,942

(22) Filed: Mar. 18, 2014

(65) Prior Publication Data

US 2014/0374603 A1    Dec. 25, 2014

Related U.S. Application Data

(60) Provisional application No. 61/837,431, filed on Jun. 20, 2013.

(51) Int. Cl.
*G01J 5/02* (2006.01)
*G01N 21/64* (2006.01)
*G01B 11/25* (2006.01)
*G01N 15/14* (2006.01)

(52) U.S. Cl.
CPC ............... *G01N 21/64* (2013.01); *G01B 11/25* (2013.01); *G01N 2015/145* (2013.01); *G01N 2021/6495* (2013.01); *G01N 2021/6497* (2013.01)

(58) Field of Classification Search
CPC . G03F 7/20; G03F 7/70625; G01N 2015/145; G01B 11/24; G01B 11/026; G01B 11/254
USPC ............................................. 250/341.1–341.8
See application file for complete search history.

(56) References Cited

U.S. PATENT DOCUMENTS

| | | | | |
|---|---|---|---|---|
| 5,306,144 | A * | 4/1994 | Hibst et al. | 433/29 |
| 5,920,390 | A | 7/1999 | Farahi et al. | |
| 6,050,656 | A | 4/2000 | Farahi et al. | |
| 6,556,706 | B1 * | 4/2003 | Geng | 382/154 |
| 6,980,710 | B2 | 12/2005 | Farahi et al. | |

(Continued)

OTHER PUBLICATIONS

Hui et al., "3D profile reconstruction of solder paste based on phse shift profilometry," 2007, IEEE, pp. 165-170.*

(Continued)

*Primary Examiner* — Kiho Kim
(74) *Attorney, Agent, or Firm* — Clements Bernard PLLC; Christopher L. Bernard; Lawrence A. Baratta, Jr.

(57) ABSTRACT

Novel measurement techniques based on moiré techniques and optical frequency conversion. For example, in the IR realm, the configuration can be any moiré configuration, the detector is an IR detector, and the light source can be at any wavelength. The optical configuration, the detector, and the type of light source depend on the physical properties of object/scene and the parameter(s) to be measured.

26 Claims, 5 Drawing Sheets

(56) References Cited

U.S. PATENT DOCUMENTS

| | | |
|---|---|---|
| 7,058,245 B2 | 6/2006 | Farahi |
| 7,067,240 B2 | 6/2006 | Farahi et al. |
| 7,126,976 B2 | 10/2006 | Farahi et al. |
| 8,463,092 B2 | 6/2013 | Farahi |
| 8,531,650 B2 * | 9/2013 | Feldkhun et al. ............ 356/4.01 |
| 2003/0203524 A1 | 10/2003 | Farahi et al. |
| 2010/0008588 A1 * | 1/2010 | Feldkhun et al. ............. 382/206 |
| 2011/0232211 A1 | 9/2011 | Farahi |
| 2013/0153651 A1 * | 6/2013 | Fedorovskaya et al. ...... 235/375 |
| 2013/0340543 A1 | 12/2013 | Farahi et al. |
| 2014/0000704 A1 | 1/2014 | Farahi |

OTHER PUBLICATIONS

Buytaert et al., Moire profilometry using liquid crystals for projection and demodulation, © 2008 Optical Society of America, Jan. 7, 2008 / vol. 16, No. 1 / Optics Express 179.

* cited by examiner

PROFILOMETRY SYSTEMS AND METHODS BASED ON ABSORPTION AND OPTICAL FREQUENCY CONVERSION

CROSS-REFERENCE TO RELATED APPLICATION

The present patent application/patent claims the benefit of priority of U.S. Provisional Patent Application No. 61/837,431, filed on Jun. 20, 2013, and entitled "PROFILOMETRY BASED ON ABSORPTION AND OPTICAL FREQUENCY CONVERSION," the contents of which are incorporated in full by reference herein.

FIELD OF THE DISCLOSURE

The present disclosure relates generally to the optical and profilometry fields. More specifically, the present disclosure relates to profilometry systems and methods based on absorption and optical frequency conversion.

BACKGROUND OF THE DISCLOSURE

Moiré techniques are optical methods for form and surface measurement and characterization. They can be used to measure in-plane deformation and strain, as well as out-of-plane deformation and profilometry. In-plane measurements are usually performed by attaching a grating to an object and then measuring the deformation of the grating. Out-of-plane measurements are usually based on illuminating the object with structured light, which is typically a straight-line grating, and measuring the deformation of reflected light from the object. In both cases, the reflected light can be summed or multiplied by another grating to form a moiré fringe pattern, or the deformation can be measured directly.

There are different moiré techniques, including fringe projection, shadow moiré, projection moiré, and reflection moiré. These are illustrated in FIG. 1.

In fringe projection, a fringe pattern (e.g. parallel lines) is projected onto the object and the projected fringe pattern is captured from another angle. The fringe pattern will be distorted according to the profile of the object. The distance between contours of acquired fringe pattern depends on the pitch of projected fringe pattern and the parameters of fringe projection setup. By analyzing the acquired fringe pattern and knowing the parameters of the fringe projection setup, the profile of the object is calculated.

Shadow moiré uses a grating in front of the object. A collimated light passes through the grating and makes a shadow of the grating on the object. This shadow is captured from different angles through the grating, which produces a moiré pattern.

Projection moiré uses two different gratings, instead of one, one in front of a collimated light source and the other one in front of a camera. The profile of the object is calculated from the moiré pattern and the parameters of the projection moiré setup.

Reflection moiré uses one grating in front of the light source. The structured light is reflected back from a specular object and captured by the camera. The deformation of the structured light (i.e. grating) is related to the slope distribution of the object profile.

What are still needed in the art, however, are profilometry systems and methods that can be used with very bright or very dark objects, with extreme levels of reflection or no reflection, using ultraviolet (UV), visible, near infrared (NIR), or infrared (IR) light and heat, or visible or UV light and fluorescence.

BRIEF SUMMARY OF THE DISCLOSURE

In various exemplary embodiments, the present disclosure provides novel measurement techniques based on moiré techniques and optical frequency conversion. For example, in the IR realm, the configuration can be any moiré configuration, the detector is an IR detector, and the light source can be at any wavelength. The optical configuration, the detector, and the type of light source depend on the physical properties of object/scene and the parameter(s) to be measured.

In one exemplary embodiment, the present invention provides a profilometry system, comprising: a radiation source for delivering radiation of a given wavelength to an object; and a detector operable for detecting resulting radiation reflected or emitted from the object; wherein a frequency of the resulting radiation is converted due to the absorption and emission of radiation by the object. Optionally, the radiation source comprises an IR radiation source and the detector comprises an IR detector. Optionally, the radiation source comprises a short wavelength (SW) radiation source, such as a UV, visible, or NIR light source and the detector comprises an IR detector. Optionally, the radiation source comprises a SW light source and the detector comprises a SW light detector and an IR detector. Optionally, the radiation source comprises a SW light source and an IR source and the detector comprises a SW light detector and an IR detector. Optionally, the delivered radiation induces fluorescence in the object. Optionally, the detector images the object at a fluorescence wavelength. Optionally, the detector images the object at a fluorescence wavelength and an original wavelength simultaneously. Optionally, the detector images the object at a fluorescence wavelength and an original wavelength successively. Optionally, the detector images the object at a fluorescence wavelength and an IR wavelength. Optionally, two detectors image the object at a fluorescence wavelength and an original wavelength, which is the SW, respectively. Optionally, two detectors image the object at a fluorescence wavelength and an IR wavelength, respectively. Optionally, two detectors image the object at a SW wavelength and an IR wavelength, respectively.

In another exemplary embodiment, the present invention provides a profilometry method, comprising: providing a radiation source for delivering radiation of a given wavelength to an object; and providing a detector operable for detecting resulting radiation reflected or emitted from the object; wherein a frequency of the resulting radiation is converted due to the absorption and emission of radiation by the object. Optionally, the radiation source comprises an IR radiation source and the detector comprises an IR detector. Optionally, the radiation source comprises a SW light source and the detector comprises an IR detector. Optionally, the radiation source comprises a SW light source and the detector comprises a SW light detector and an IR detector. Optionally, the radiation source comprises a SW light source and an IR source and the detector comprises a SW light detector and an IR detector. Optionally, the delivered radiation induces fluorescence in the object. Optionally, the detector images the object at a fluorescence wavelength. Optionally, the detector images the object at a fluorescence wavelength and an original wavelength simultaneously. Optionally, the detector images the object at a fluorescence wavelength and an original wavelength successively. Optionally, the detector images the object at a fluorescence wavelength and an IR wavelength.

Optionally, two detectors image the object at a fluorescence wavelength and an original wavelength, which is the SW, respectively. Optionally, two detectors image the object at a fluorescence wavelength and an IR wavelength, respectively. Optionally, two detectors image the object at a SW wavelength and an IR wavelength, respectively.

BRIEF DESCRIPTION OF THE DRAWINGS

The present invention is illustrated and described herein with reference to the various drawings, in which like reference numbers are used to denote like system components/method steps, as appropriate, and in which.

DETAILED DESCRIPTION OF THE DISCLOSURE

Again, in various exemplary embodiments, the present disclosure provides novel measurement techniques based on moiré techniques and optical frequency conversion. For example, in the IR realm, the configuration can be any moiré configuration, the detector is an IR detector, and the light source can be at any wavelength. The optical configuration, the detector, and the type of light source depend on the physical properties of object/scene and the parameter(s) to be measured. The profilometry systems and methods of the present disclosure can be used with very bright or very dark objects, with extreme levels of reflection or no reflection, using SW or IR light and heat, or visible or UV light and fluorescence.

The present disclosure provides novel systems and methods using moirétechniques and optical frequency conversion due to the absorption and emission process of the object to be measured. A detector array then selectively collects a signal at this new frequency or collectively gathers a signal at the excitation, as well as the emission and reflection wavelength. Two distinct examples are provided herein below.

Figure 1A:
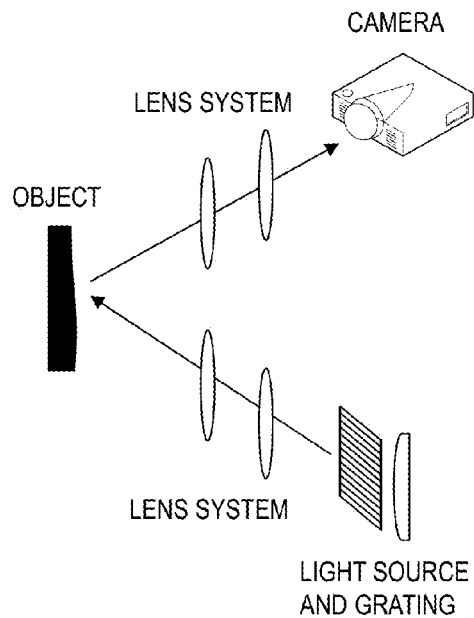
FIG. 1 is a series of schematic diagrams illustrating moiré techniques—(a) fringe projection, (b) shadow moiré, (c) projection moiré, and (d) reflection moiré.
Figure 1B:
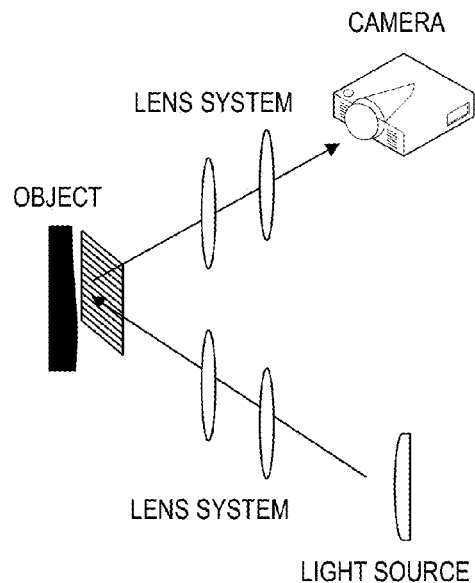
Figure 1C:
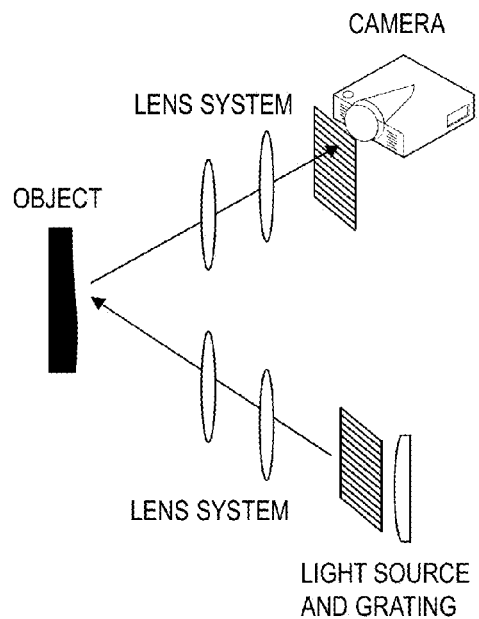
Figure 1D:
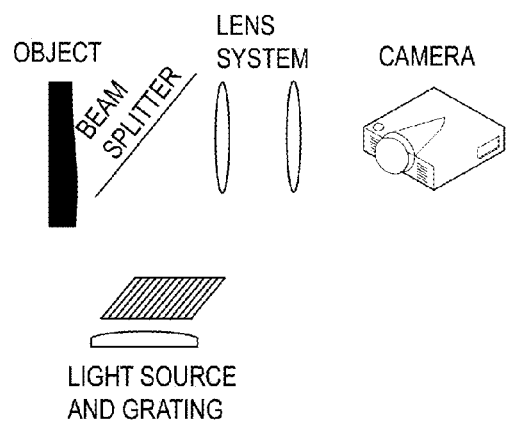
Figure 2:
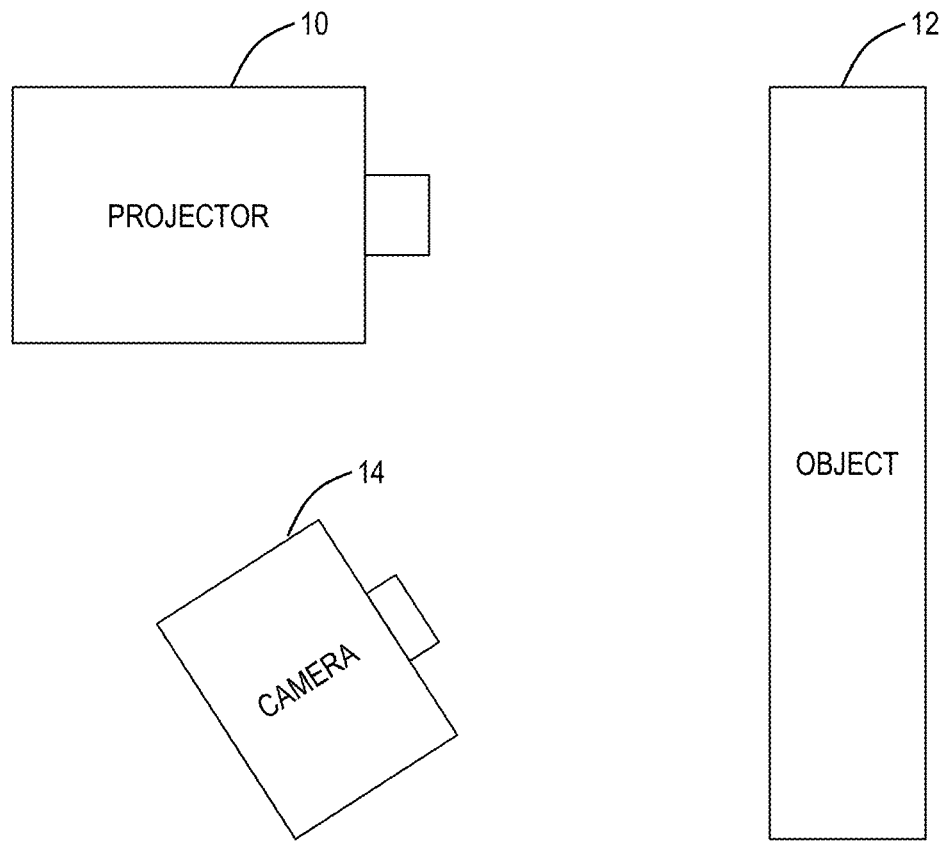
FIG. 2 is a schematic diagram illustrating an experimental setup for an IR-moiré technique with fringe projection in accordance with the present disclosure.

Referring specifically to FIG. 2, in the first example, light from a light source 10 is used to illuminate an object 12 and generate heat (in the IR region of the optical spectrum), which is then observed using an IR camera 14. In the second example, emitted light from the light source 10 induces fluorescence in the object 12, which fluorescent signal is in turn observed by the camera 14. This is beneficial in cases where there is very low or no reflected light from the surface of the object 12. This is true for optical dark surfaces.

The configuration for the IR-moiré of the present disclosure is the same as a conventional moiré technique. Therefore, the schemes that are illustrated in FIG. 1 are some examples that are equally applicable here.

The light source 10 for IR moiré can be an IR source (e.g. and IR projector, like the DLP Light Commander Development Kit) or a source at another wavelength that can be absorbed by the object and converted into the heat (e.g. a conventional projector). The projected fringe pattern then can be captured using the IR camera 14 or the like (for example a Tamarisk 320 IR camera).

If a source out of the IR spectrum range is used as the light source 10 (e.g. UV, visible, or NIR light), part of the incident light on the surface of the object will be converted to heat (i.e. IR radiation), which will be detectable using an IR camera 14.

The amount of light absorption, or the percentage of absorbed light that is converted into heat, and the distribution of heat on the surface of the object as a function of time have to be considered to project proper fringe patterns, acquire proper moiré patterns, and calculate the accurate profile of the object.

This technique can be combined with a conventional moiré technique to acquire a profile of the object with the aid of combined techniques.

Figure 3A:
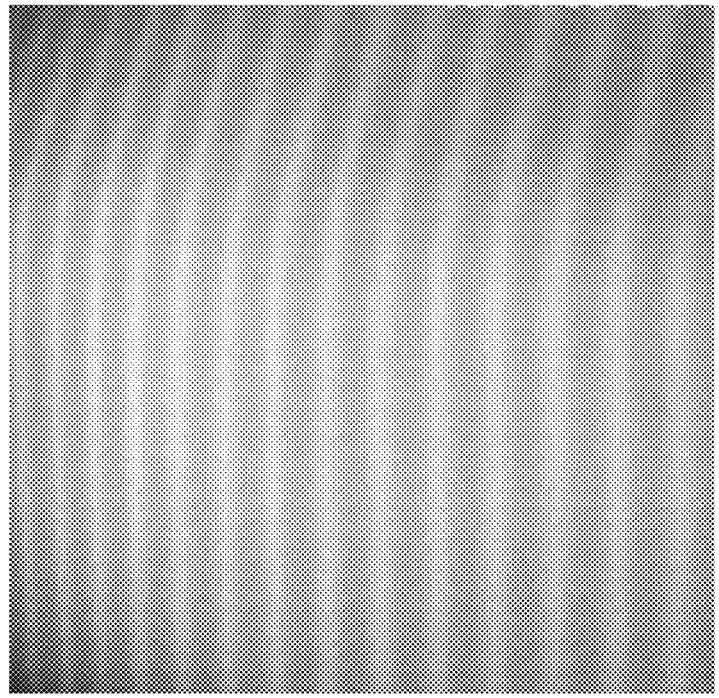
FIG. 3 illustrates a fringe pattern for two objects using the IR-moiré technique of the present disclosure—(a) folded black cardboard and (b) egg holder-shaped object.
Figure 3B:
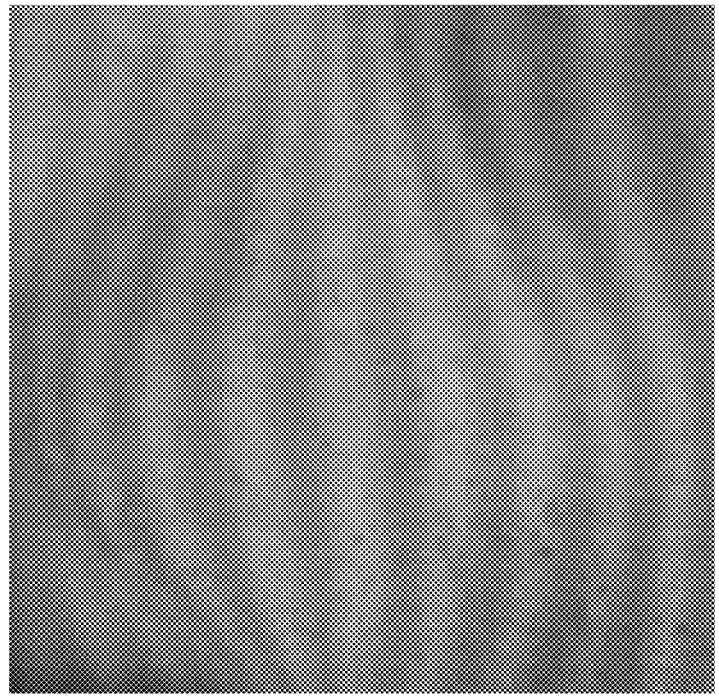
Figure 4A:
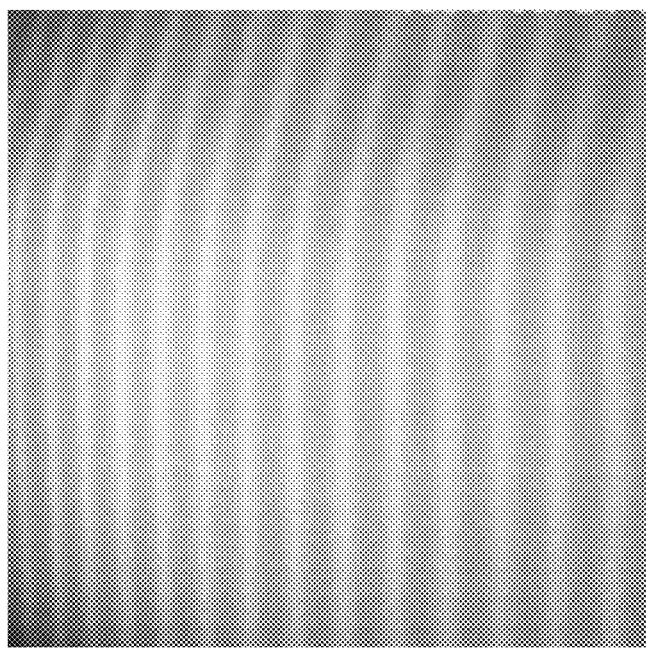
FIG. 4 illustrates a reconstructed profile for two objects from fringe patterns acquired using the IR-moiré technique of the present disclosure—(a) folded black cardboard and (b) egg holder-shaped object.
Figure 4A:
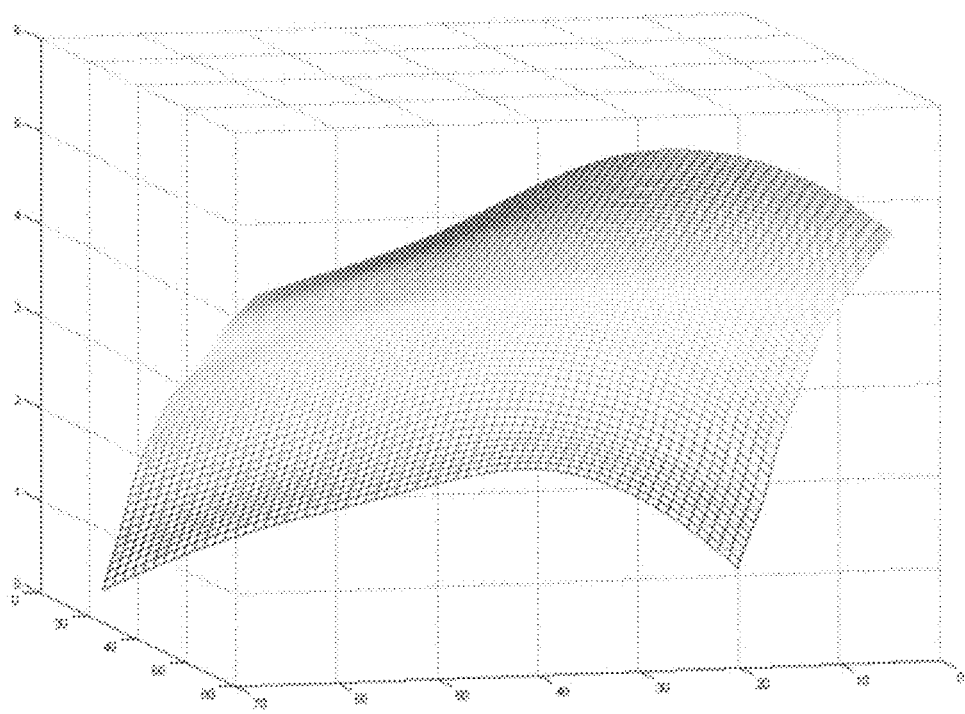
Figure 4B:
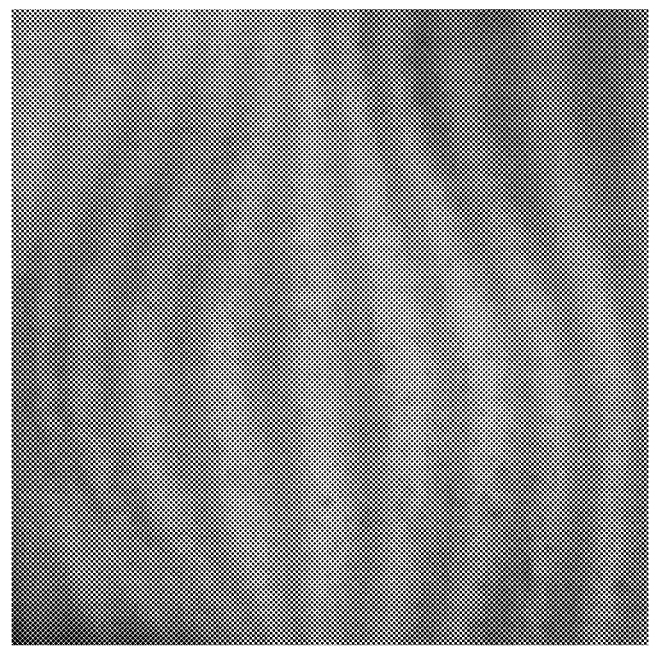
Figure 4B:
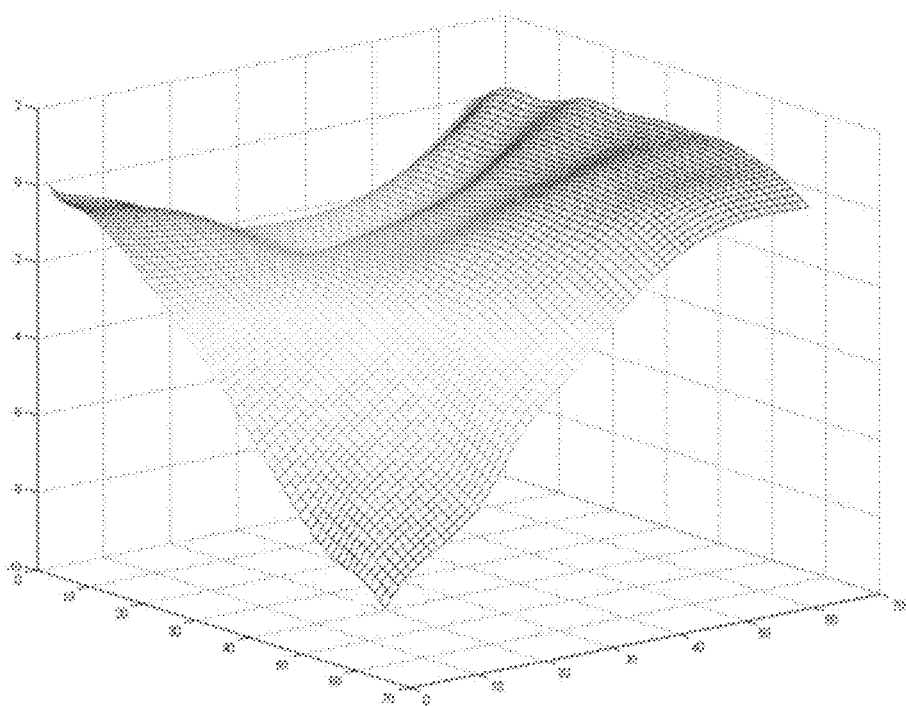

To show the feasibility of the IR-moiré technique, the following experiment was conducted. A conventional projector in the visible wavelength range was used to project the fringe pattern. The heat generated by the absorbed light emitted IR light (i.e. heat) that was captured by the IR camera. FIG. 3 shows the captured fringe pattern for a folded black cardboard (a) and an egg holder-shaped object (b).

As is seen, the projected patterns are formed on the object and then captured using the IR camera. Since the formed fringe patterns are the same as the acquired fringe patterns in conventional moiré techniques, the same fringe analysis can be used to calculate the profile of the object. FIG. 4 shows the calculated profiles from the acquired fringe patterns.

Depending on the mechanism of the fringe formation in IR-moiré techniques, the fringe analysis techniques for conventional moiré techniques might need some modifications or some new fringe analysis techniques might be needed.

For some dark objects, it is impossible to measure their profile using visible light as a result of high absorption in the visible spectrum. We can use an IR-moiré technique that uses a SW light source to generate an IR wavelength at the object to measure the profile of dark objects using IR wavelengths.

The configuration for fluorescent-moiré is the same as other moiré systems. Therefore, the schemes that are shown in FIG. 1 are some examples of fluorescent-moiré technique configurations.

The light source for fluorescent-moiré can be at any wavelength, from x-ray to deep IR, which can be absorbed by the object and induces excitation and fluorescence emission. The projected fringe pattern then can be captured using a camera that is sensitive to a fluorescent signal. The original light that is reflected back from the object may or may not be filtered out.

The amount of light absorption, percentage of absorbed light that is converted into a fluorescent signal, and the secondary excitation effect (the fluorescence caused by the new frequency down converted signal on the regions that originally were not exposed to light) have to be considered to project a proper fringe pattern, acquire a proper moiré pattern, and calculate the accurate profile of the object.

Again, this technique can be combined with a conventional moiré technique to acquire a profile of the object with the aid of combined techniques.

Although the present disclosure is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A profilometry system, comprising:
a radiation source for delivering a structured radiation pattern to an object, wherein the structured radiation pattern has a first frequency content; and
a detector operable for detecting a resulting deformed radiation pattern reflected or emitted from the object, wherein the resulting deformed radiation pattern has a second different frequency content and a different spatial configuration;
wherein a conversion from the structured radiation pattern to the resulting deformed radiation pattern and a corresponding conversion from the first frequency content to the second different frequency content are due to the absorption and emission of radiation by the object;
wherein the first frequency content comprises one of an ultraviolet wavelength, a visible wavelength, a near-infrared wavelength, and an infrared wavelength; and
wherein the second different frequency content comprises one of a different ultraviolet wavelength, a different visible wavelength, a different near-infrared wavelength, and a different infrared wavelength.

2. The profilometry system of claim 1, wherein the radiation source comprises an IR radiation source and the detector comprises an IR detector.

3. The profilometry system of claim 1, wherein the radiation source comprises a short wavelength light source and the detector comprises an IR detector.

4. The profilometry system of claim 1, wherein the radiation source comprises a short wavelength light source and the detector comprises a short wavelength light detector and an IR detector.

5. The profilometry system of claim 1, wherein the radiation source comprises a short wavelength light source and an IR source and the detector comprises a short wavelength light detector and an IR detector.

6. The profilometry system of claim 1, wherein the delivered radiation causes fluorescence in the object.

7. The profilometry system of claim 6, wherein the detector captures the pattern at a fluorescence wavelength.

8. The profilometry system of claim 7, wherein the detector captures the pattern at a fluorescence wavelength and an original wavelength simultaneously.

9. The profilometry system of claim 7, wherein the detector captures the pattern at a fluorescence wavelength and an original wavelength successively.

10. The profilometry system of claim 7, wherein the detector captures the pattern at a fluorescence wavelength and an IR wavelength.

11. The profilometry system of claim 6, wherein two or more detectors capture the pattern:
at a fluorescence wavelength and a short wavelength, respectively; or
at a fluorescence wavelength and an IR wavelength, respectively.

12. The profilometry system of claim 1, wherein two or more detectors capture the pattern:
at a short wavelength and an IR wavelength, respectively.

13. The profilometry system of claim 1, wherein the captured patterns are combined to form a pattern with enhanced dynamic range.

14. A profilometry method, comprising:
providing a radiation source for delivering a structured radiation pattern to an object, wherein the structured radiation pattern has a first frequency content; and
providing a detector operable for detecting a resulting deformed radiation pattern reflected or emitted from the object, wherein the resulting deformed radiation pattern has a second different frequency content and a different spatial configuration;
wherein a conversion from the structured radiation pattern to the resulting deformed radiation pattern and a corresponding conversion from the first frequency content to the second different frequency content are due to the absorption and emission of radiation by the object;
wherein the first frequency content comprises one of an ultraviolet wavelength, a visible wavelength, a near-infrared wavelength, and an infrared wavelength; and
wherein the second different frequency content comprises one of a different ultraviolet wavelength, a different visible wavelength, a different near-infrared wavelength, and a different infrared wavelength.

15. The profilometry method of claim 14, wherein the radiation source comprises an IR radiation source and the detector comprises an IR detector.

16. The profilometry method of claim 14, wherein the radiation source comprises a short wavelength light source and the detector comprises an IR detector.

17. The profilometry method of claim 14, wherein the radiation source comprises a short wavelength light source and the detector comprises a short wavelength light detector and an IR detector.

18. The profilometry method of claim 14, wherein the radiation source comprises a short wavelength light source and an IR source and the detector comprises a short wavelength light detector and an IR detector.

19. The profilometry method of claim 14, wherein the delivered radiation causes fluorescence in the object.

20. The profilometry method of claim 19, wherein the detector captures the pattern at a fluorescence wavelength.

21. The profilometry method of claim 20, wherein the detector captures the pattern at a fluorescence wavelength and an original wavelength simultaneously.

22. The profilometry method of claim 20, wherein the detector captures the pattern at a fluorescence wavelength and an original wavelength successively.

23. The profilometry method of claim 20, wherein the detector captures the pattern at a fluorescence wavelength and an IR wavelength.

24. The profilometry method of claim 20, wherein two or more detectors capture the pattern:
at a fluorescence wavelength and a short wavelength, respectively; or
at a fluorescence wavelength and an IR wavelength, respectively.

25. The profilometry method of claim 14, wherein two or more detectors capture the pattern:
at a short wavelength and an IR wavelength, respectively.

26. The profilometry method of claim 14, wherein the captured patterns are combined to form a pattern with enhanced dynamic range.

* * * * *